(12) United States Patent
Brumfield et al.

(10) Patent No.: US 12,171,588 B2
(45) Date of Patent: Dec. 24, 2024

(54) STERILE SURGICAL IMPLANT HOLDER

(71) Applicant: Ingeniumspine, LLC, Phoenix, AZ (US)

(72) Inventors: David Brumfield, Collierville, TN (US); B. Thomas Barker, Bartlett, TN (US); Murali Kadaba, Austin, TX (US); Dennis Crandall, Mesa, AZ (US)

(73) Assignee: Ingeniumspine, LLC

( * ) Notice: Subject to any disclaimer, the term of this patent is extended or adjusted under 35 U.S.C. 154(b) by 0 days.

(21) Appl. No.: 18/429,162

(22) Filed: Jan. 31, 2024

(65) Prior Publication Data

US 2024/0390094 A1 Nov. 28, 2024

Related U.S. Application Data

(63) Continuation of application No. 18/201,623, filed on May 24, 2023, now Pat. No. 11,925,491.

(51) Int. Cl.
*A61B 50/30* (2016.01)
*A61B 17/70* (2006.01)

(52) U.S. Cl.
CPC .......... *A61B 50/30* (2016.02); *A61B 17/7071* (2013.01); *A61B 2050/3008* (2016.02); *A61B 2050/314* (2016.02)

(58) Field of Classification Search
CPC ................ A61B 50/30; A61B 17/7071; A61B 2050/3008; A61B 2050/314

USPC .............................................................. 606/1
See application file for complete search history.

(56) References Cited

U.S. PATENT DOCUMENTS

| | | | |
|---|---|---|---|
| 2003/0118424 A1* | 6/2003 | Obermeier | F16B 27/00 411/442 |
| 2014/0309702 A1* | 10/2014 | Wand | A61B 50/20 206/339 |
| 2016/0228188 A1* | 8/2016 | Sweeney | A61B 50/30 |

* cited by examiner

*Primary Examiner* — Aaron F Roane
(74) *Attorney, Agent, or Firm* — Etherton Law Group, LLC

(57) ABSTRACT

A sterile holder for sterile surgical implants. The implant holder is an ergonomically shaped body of deformable material having an implant-receiving cavity similar in size and shape to the implant. To remove the implant from the holder, the surgeon mates a sterile tool to the implant and gently pries the implant out of the holder by deforming the body. Preferably the tool used to pry the implant out of the body is an insertion tool mated to the implant which is also used to insert the implant in a patient. In this way the surgeon retrieves the implant from its container without touching the container and directly inserts the implant in the patient without risking contamination: sterility is maintained for both the surgeon and the implant. In a preferred embodiment, the implant holder is configured to hold two pedicle screws and their set-screws.

19 Claims, 10 Drawing Sheets

STERILE SURGICAL IMPLANT HOLDER

CROSS-REFERENCE TO RELATED APPLICATIONS

This application claims the benefit of co-pending U.S. application Ser. No. 18/201,623 filed May 24, 2023.

FIELD OF INVENTION

The present invention relates generally to devices for holding sterile surgical implants which enable the implants to be extracted from the holder in a sterile manner.

BACKGROUND

In spinal fusion procedures various devices are implanted into the patient's body to join adjacent vertebrae with the goal of maintaining spine alignment and intervertebral separation. These devices most commonly include pedicle screws, which are screwed into the vertebrae to support titanium rods that are held in place by the screws.

Although the general shape of vertebrae are common between patients, the specific size, shape, lordosis, and condition of the vertebrae are peculiar to each patient. These biological factors affect the size, shape and placement of the implanted devices. Radiographs can give the surgeons a good idea of a given patient's condition prior to surgery, but sometimes the in vivo observation reveals unexpected factors, such as severe areas of necrotic, sclerotic, osteoporotic or cancerous bone as well as trajectories of pedicle screws from previous or current surgeries, which may prevent the surgeon from placing the anchor in a desired direction and location. Consequently, a surgeon needs an array of implants of various dimensions from which the surgeon can choose the appropriate ones during surgery.

Implant sets are commercially available, with multiple sizes of screws, set screws, rods, connectors, plates, pins and other implants and instruments. The implants are typically provided in a sterile tray containing an array of about 150 implant sizes and instrumentation. A surgeon typically opens a tray and chooses implants needed for that particular surgery. For pedicle screws, usually four or more are needed per surgery. The pedicle screws are removed from the implant tray and are attached to the screw driver by a surgical technician. The manual handling of the pedicle screw may unfortunately expose the implants to contamination potentially leading to infection. Recent studies have shown that up to about 5 to 18% of spinal fusion surgeries results in infection. In addition to the health cost to the infected patient, the monetary cost of such infections can be two to three times the cost of original surgery.

After the surgery, the implant salesman adds new screws to the implant tray to replace the screws that were used during surgery. Then the implant tray is sterilized. Consequently, screws that are not used in surgery, such as odd-sized screws, may be subjected to sterilization repeatedly.

One method to decrease the likelihood of contamination is to package each implant in a double container. For example, a pedicle screw may be packaged in an inner envelope or tube which is packaged in an outer envelope, all in an aseptic environment. A selection of double-wrapped pedicle screws is delivered to the operating room. The outer containers arrive contaminated from transit. It is important to avoid any risk of contamination by direct or indirect contact between this outer container and the inner container or even the product itself. For the envelope version, this is accomplished by a person opening the contaminated outer envelope, exposing the sterile inner envelope, and dropping the inner envelope on a sterile instrument tray. A second person, such as a sterile surgical technician or surgeon, grasps the inner envelope to remove the sterile implant. With the tube version, a person opens the outer tube exposing the inner tube. The sterile person removes this inner tube from the outer tube, opens the inner tube and removes the implant. The disadvantage of these approaches is that they are unwieldy, and the sterile person or surgeon touches the inner envelope or tube and the implant, risking contamination. It would be desirable to have implant systems that eliminate the need for a person to touch the implant.

SUMMARY OF THE INVENTION

This sterile holder for sterile surgical implants eliminates the need for a sterile person to touch the implant. The implant holder is an ergonomically shaped body of deformable material having an implant-receiving cavity similar in size and shape to the implant. To remove the implant from the holder, the surgeon mates a sterile tool to the implant and gently pries the implant out of the holder by deforming the body of the implant holder. Preferably the tool used to pry the implant out of the body is an insertion tool that is also used to insert the implant in a patient. In this way the surgeon retrieves the implant from its container without touching the implant and directly inserts the implant in the patient without risking contamination: sterility is maintained for both the surgeon and the implant. In a preferred embodiment, the implant holder is configured to hold two pedicle screws and two set-screws.

DETAILED DESCRIPTION OF THE INVENTION

Figure 1:
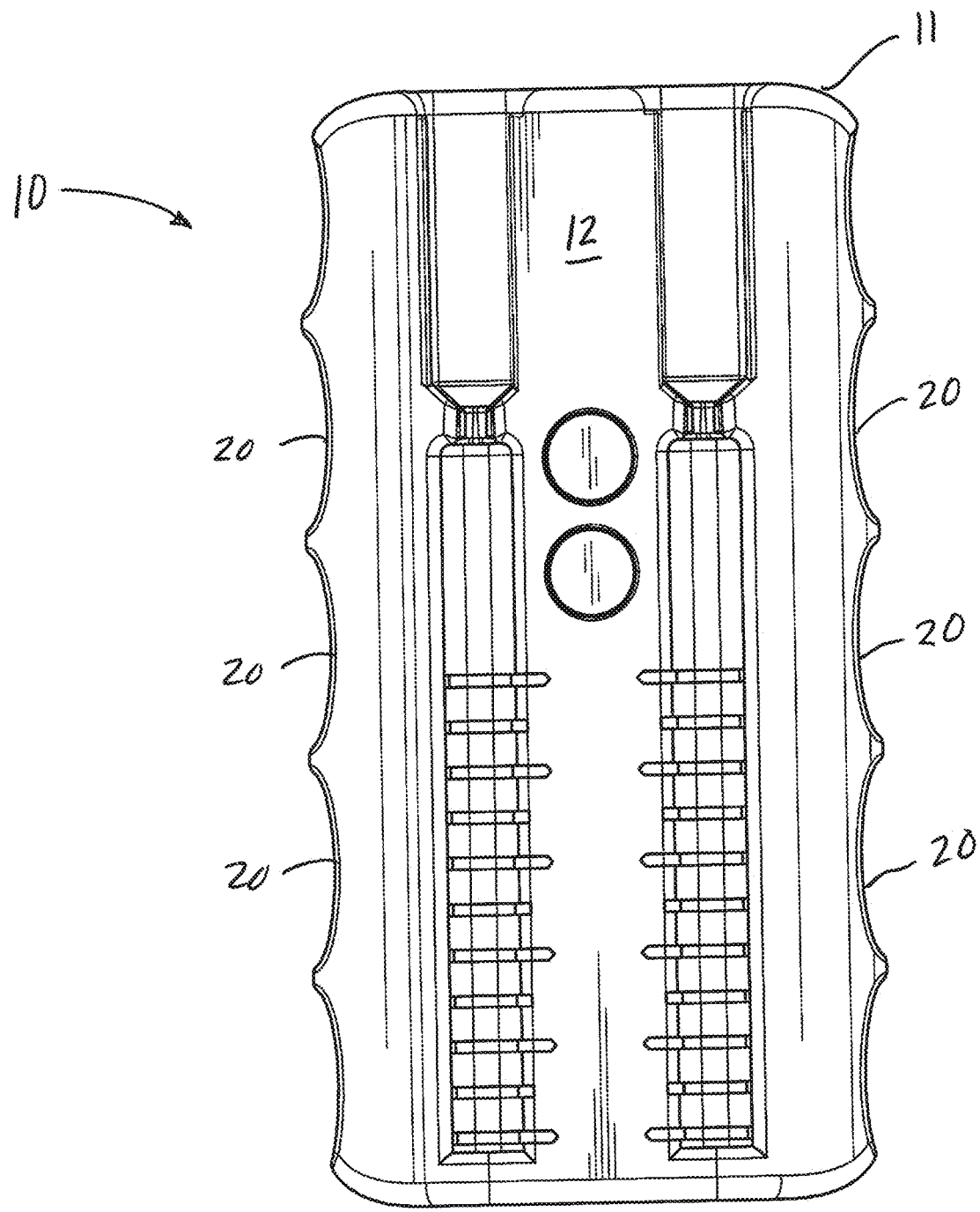
FIG. 1 is a front view of pedicle screw holder of the present invention.
Figure 2:
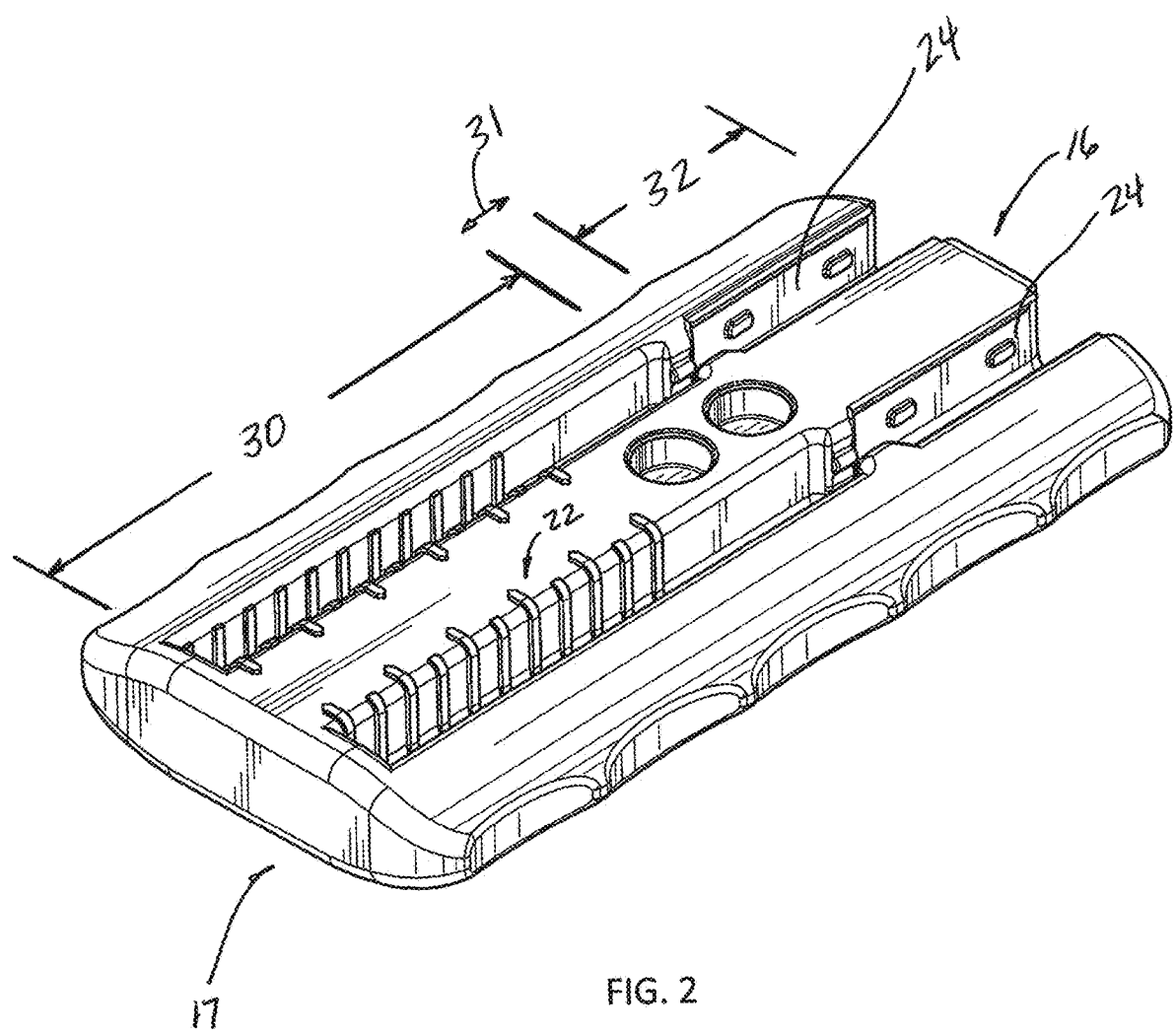
FIG. 2 is a perspective view of the pedicle screw holder of FIG. 1 viewed from the proximal end.
Figure 3:
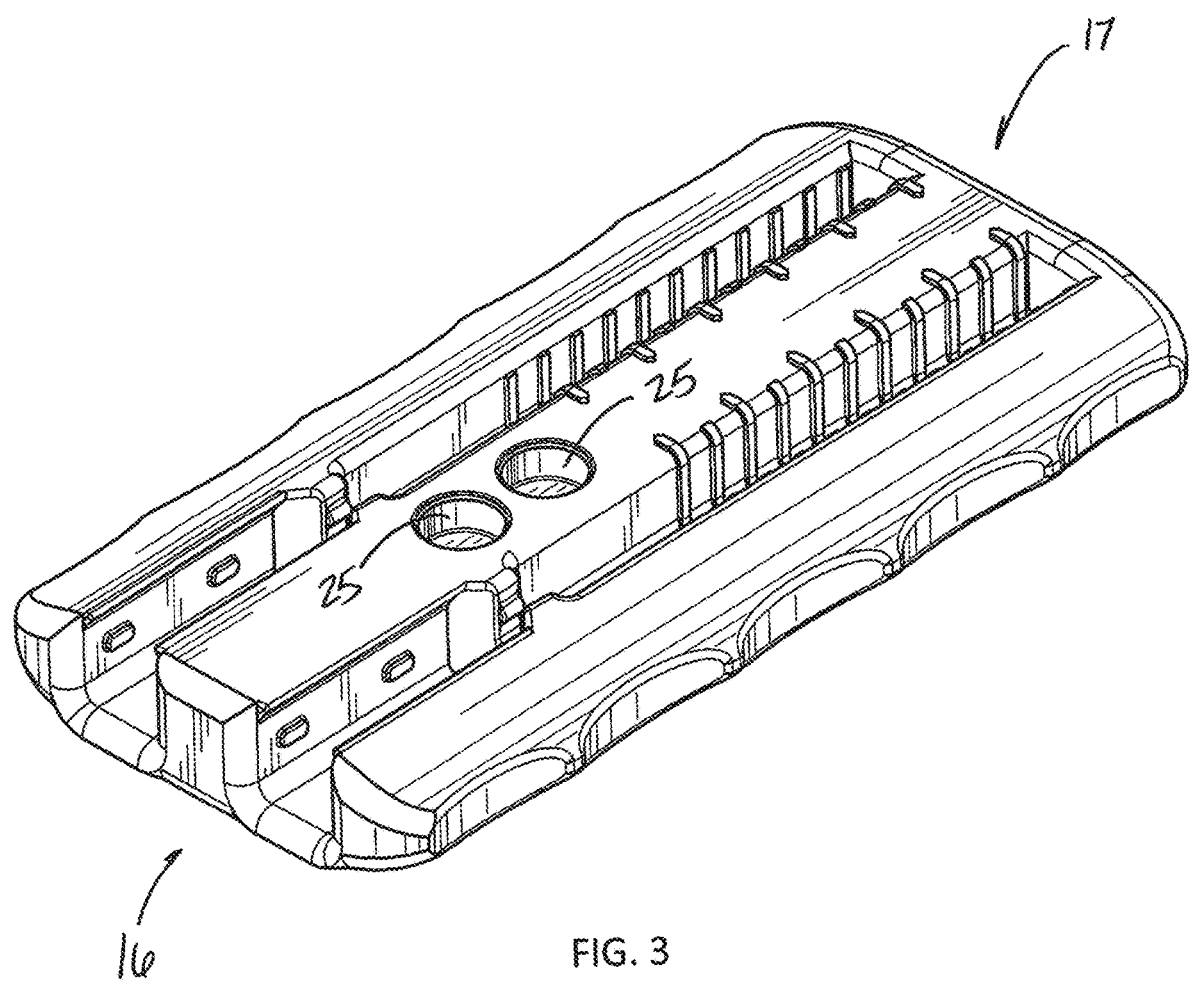
FIG. 3 is a perspective view of the pedicle screw holder of FIG. 1 viewed from the distal end.
Figure 4:
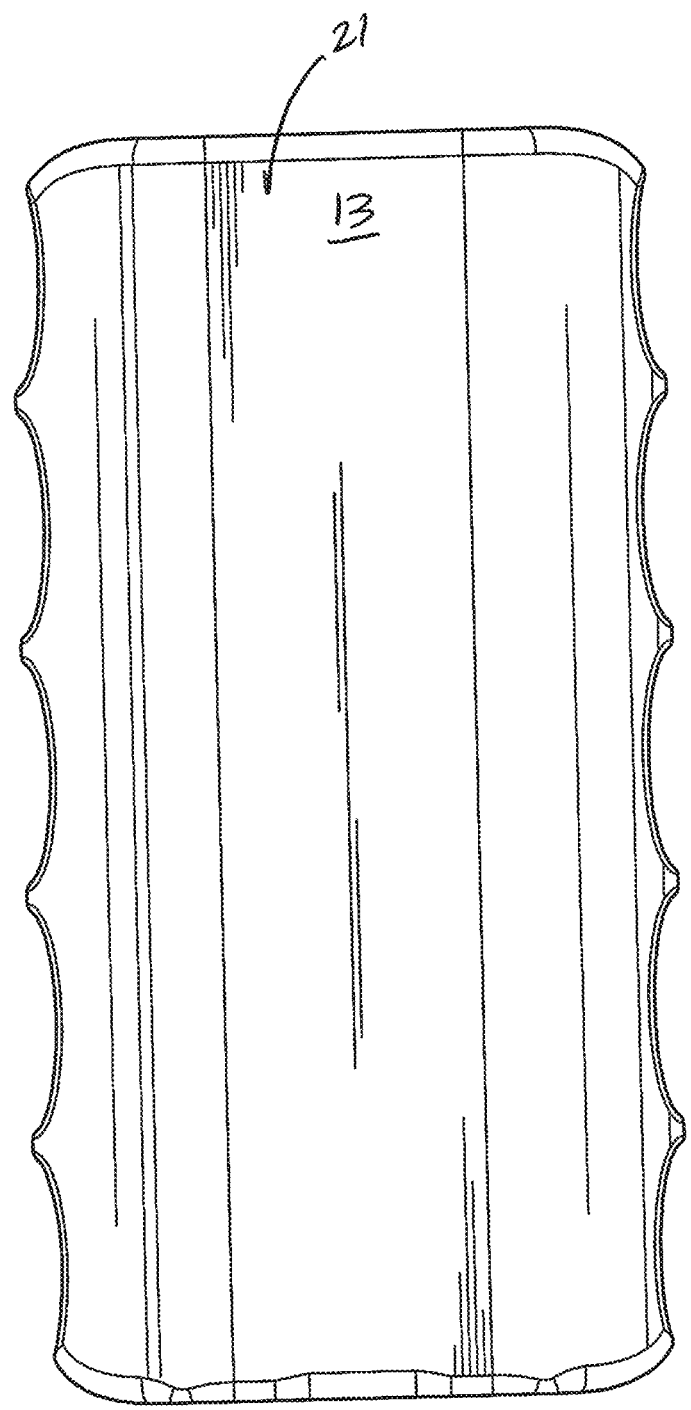
FIG. 4 is a back view of pedicle screw holder of FIG. 1.

This sterile surgical implant holder enables the surgeon to retrieve a sterile implant from its sterile container without touching the implant with his or her hands. The holder has a deformable body that has a face surface, a bottom surface, a first side, a second side, a distal end and a proximal end. The body has at least one implant-receiving cavity that is open to the face surface and configured to releasably hold an implant. The cavity is similar in size and shape to the implant. The holder may be used for any type of implant or instrument including pedicle screws, set screws, rods, connectors, hooks, spinal cages, etc. The open portion, or aperture, of the receiving cavity is smaller than the implant in length or width, or both, such that the receiving cavity covers a portion of the implant so that it doesn't fall out of the receiving cavity if the body is turned upside down. However because the body is deformable, the portion that covers the implant on the face surface can be forced to move or expand by applying pressure to the body, so that the implant can be easily pried out of the cavity by deforming the body.

To maintain sterility of the implant holder and the implant, a sterile implant is loaded into a sterile body in a sterile field by deforming the body. The loaded sterile body is encased in a sterile field in an outer wrap that will keep the holder and implants sterile during storage and transport. The outer wrap may be labeled to indicate the type of implant in the holder, by use, size, materials or other characteristic. Alternatively, an array of wrapped, loaded bodies can be stored in a reusable compartmentalized storage bin with each compartment labeled to indicate the type of implant in each compartment by use, size, materials or other characteristic. By using labeled packages or labeled compartments the unused sterile implants are not opened unless needed and are not contaminated during surgery, so they can be provided for another surgery without the need for sterilization. This reduces waste while maintaining safety.

The wrapped, loaded bodies are transported eventually to the operating room. Inside the operating room, a surgical technician opens the now-contaminated outer wrap of the desired size of screw to expose the loaded body. The technician holds the loaded body in his or her hand in arm's length of the surgeon, for easy access by the surgeon. The surgeon mates a sterile tool to the implant and gently pries the implant out of the holder by deforming the body. Preferably the tool used to pry the implant out of the body is an insertion tool mated to the implant which is also used to insert the implant in a patient's body. In this way the surgeon retrieves the implant from its container without touching the implant and directly inserts the implant in the patient without risking contamination: sterility is maintained for both the surgeon and the implant.

The body is designed to be securely held by a technician or to rest securely on a hospital instrument stand, and preferably both. In a preferred embodiment, the body is ergonomically designed to rest comfortably and securely in the palm of a surgery technician's hand to reduce the risk of dropping the body or otherwise touching it to anything that might contaminate it. For example, one or more sides of the body 11 may have grip indentations for the technician's fingers to comfortably and securely grip the body. At least a portion of the bottom surface is flat so that it rests comfortably in the technician's palm or flat on a hospital instrument stand. The body may have knurled portions on the surface to prevent the body from slipping out of the technician's hand or move about the instrument stand.

The holder is made of a deformable material. In addition to being deformable, the material is preferably also elastic, returning to its original shape after it has been deformed. The holder is preferably made of silicone, but other sterilizable elastomeric materials may be used. The holders 10 may be sterilized and reused, but preferably are disposed of after a single use.

The holder can be used for any surgical implant and is best used for implants that needs to remain sterile. In the following example the invention is presented as a kit for pedicle screws. A pedicle screw 3 has a threaded shaft 4, a U- or tulip-shaped head 5 to receive a rod, and a set screw, referred to herein as a plug 6, that fits into the head 5 to secure the rod to the head. The head 5 meets the shaft 4 at a neck 7. The implants are made of biocompatible materials including titanium, titanium alloys, cobalt-chromium alloys, or medical grade stainless steel.

The holder 10 has a deformable body 11 that has a face surface 12, a bottom surface 13, a first side 14, a second side 15, a distal end 16 and a proximal end 17. The body is generally rectangular with grip indentations 20 on both sides of the body 11. FIGS. 1-4 shows the pedicle screw holder 10. The body 11 has two screw-receiving cavities 24, each configured in the general shape of a pedicle screw, with a shaft portion 30, a neck portion 31, and a tulip portion 32. See FIG. 2. Each screw-receiving cavity 24 is open at the distal end 16 of the body 11 so that a mated screw driver can be threaded into the head 5 and pry the screw 3 out of the body 11 by deforming the body 11. The body 11 has two set-screw-receiving cavities, each configured in the general shape of a plug 6. These circular cavities are referred to herein as plug-receiving cavities 25. Similarly a screw driver mated to the plugs 6 is connected into the plug 6 to pry it out of the body 11 by deforming the body 11.

The length of the pedicle screw shaft 4, its diameter, type and spacing of the threads, and the size of the head 5 vary depending on the need of the patient at each location the screw will be inserted. Thus the surgeon needs to choose the desired size screw while surgery is ongoing. The holder is a universal size that can accommodate all sizes of screws 3 and plugs 6, which makes manufacturing easier and reduces cost. To facilitate knowing which size screw is loaded into the holder, a graduated scale 22 runs along each shaft portion 30 on the holder. Numerals that indicate the length of the shaft may be formed into the body 11 or printed on it. Shorter screws will leave the proximal end of the screw-receiving cavity empty, and the longest screws will fill the screw-receiving cavity to the proximal end.

The shaft portion 30 and a tulip portion 32 of the screw-receiving cavity 24 are universally sized to accommodate all sizes of screws 3 and plugs 6. For pedicle screw shafts that are small, that means that the shaft 4 and head 5 may not fit snugly in the screw-receiving cavity 24. To prevent all sizes of screws from falling out of the cavity, the opening in the neck portion 31 is small enough to hold all size screws in the screw-receiving cavity 24 such that even with only the neck portion 31 retaining the screw 3 in the screw-receiving cavity, the screw doesn't fall out of the holder when it is turned upside down.

Figure 5:
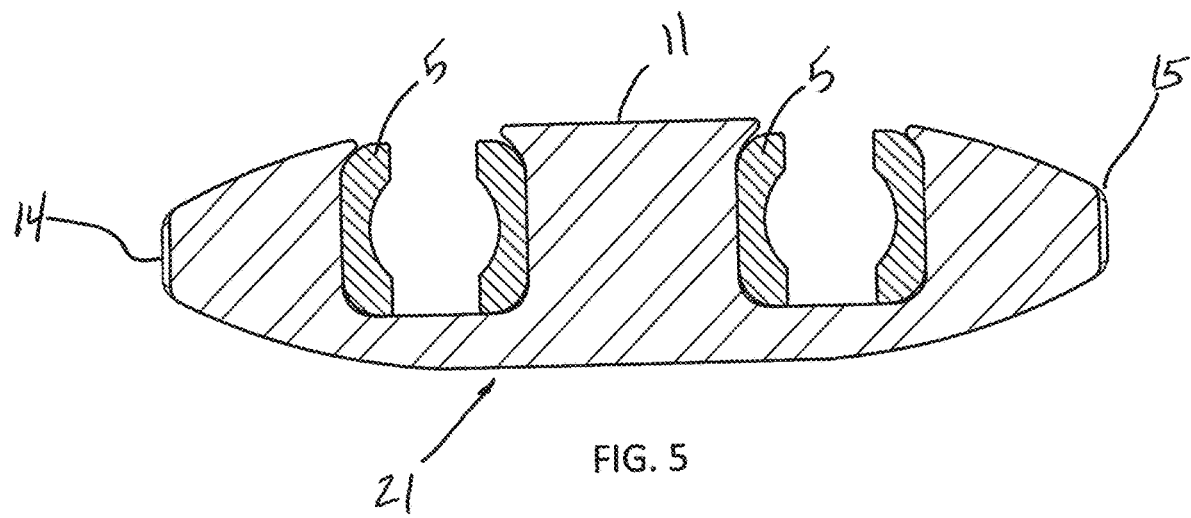
FIG. 5 is a cross-section view taken along line 5-5 of FIG. 7.
Figure 6:
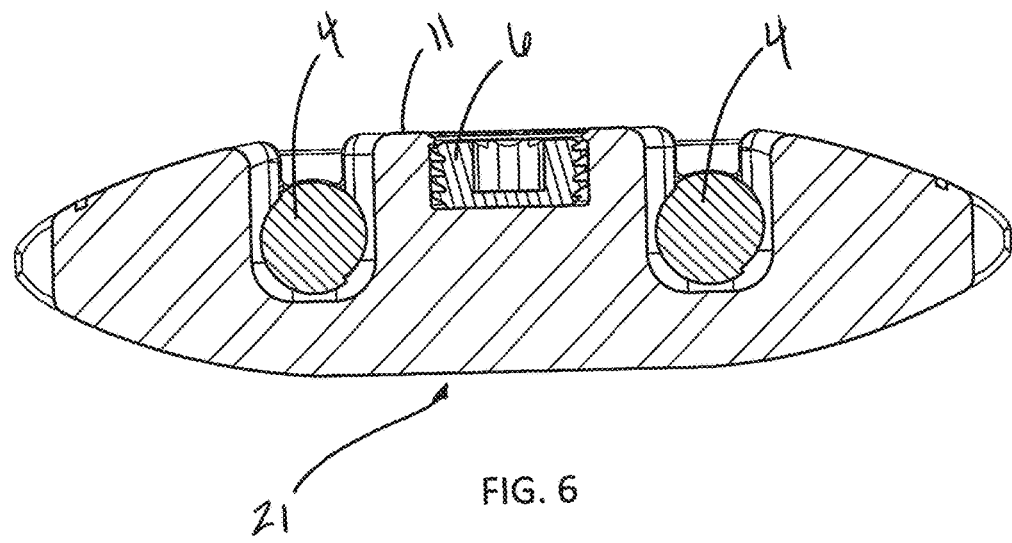
FIG. 6 is a cross-section view taken along line 6-6 of FIG. 7.

A portion 21 on the bottom 13 is flat to help keep the holder 10 from moving around on an instrument table. See FIG. 4. The flat portion 21 may be less than the entire bottom 13, as best shown in FIGS. 5 and 6, where the body 11 is slightly upturned near each side to more comfortably and securely fit in a technician's hand. Alternatively the flat portion may extend to the entire bottom 13.

Figure 7:
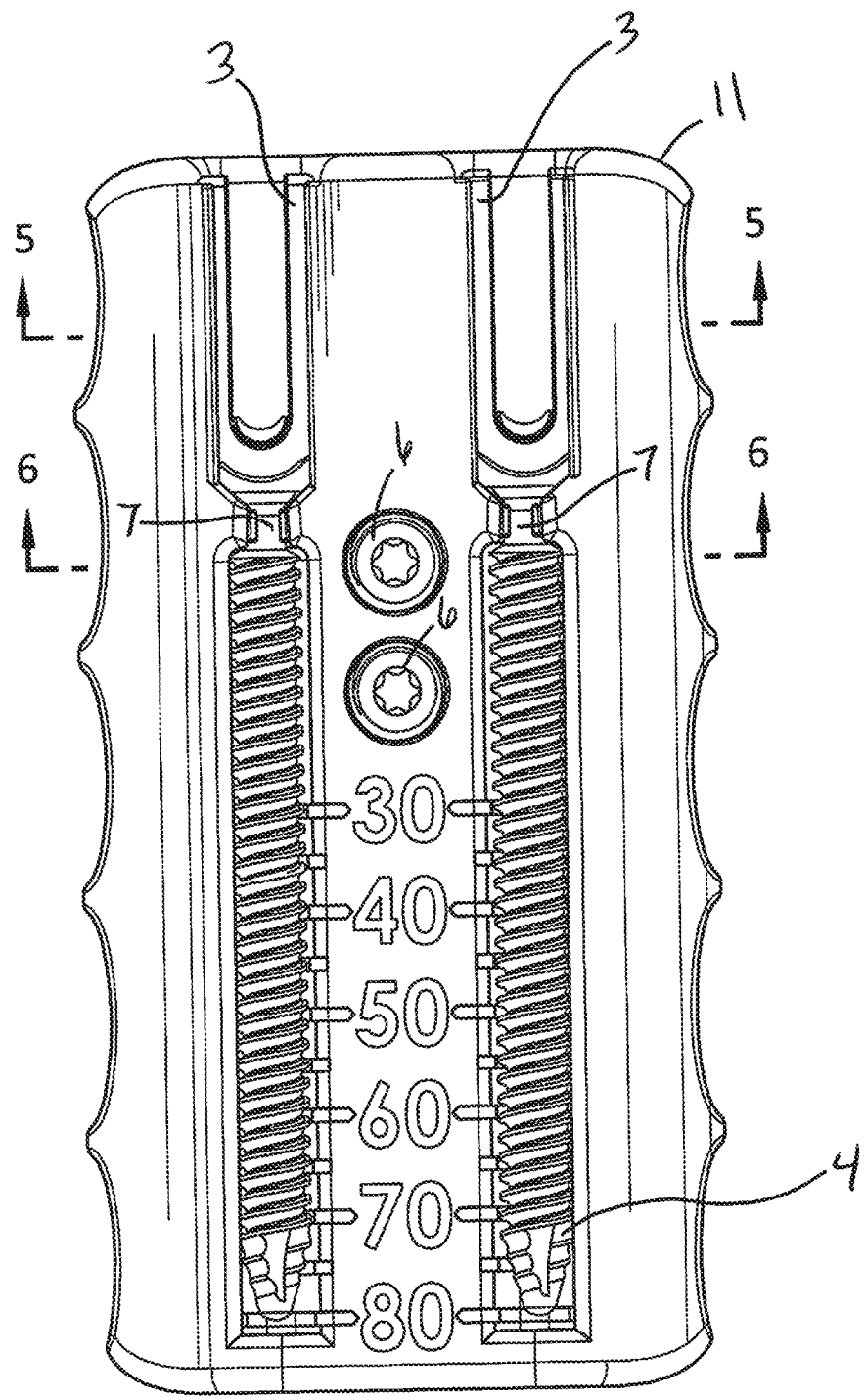
FIG. 7 is a front view of the pedicle screw holder of FIG. 1 loaded with two pedicle screws and two plugs.
Figure 8:
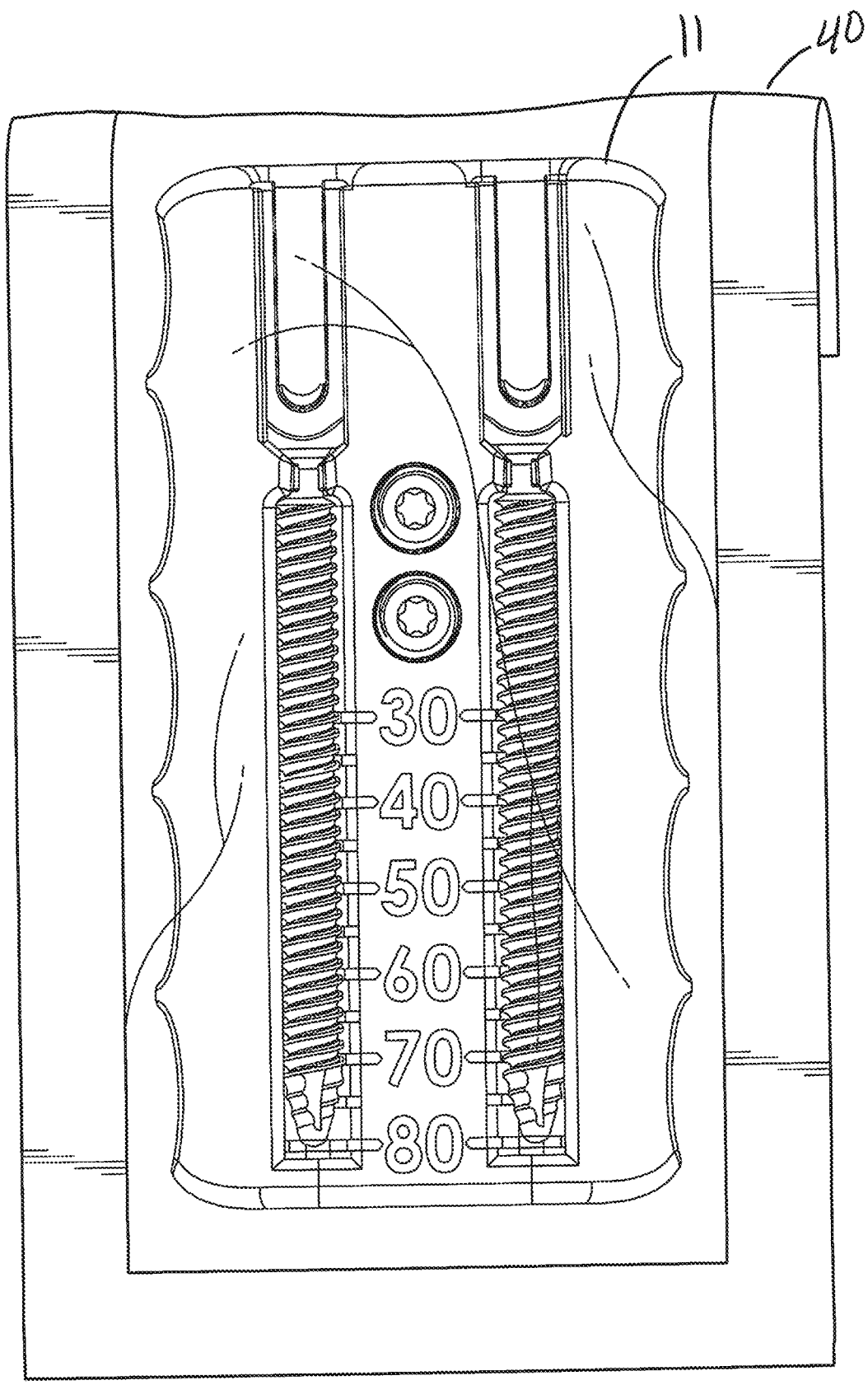
FIG. 8 is a front view of the loaded pedicle screw holder of FIG. 7 inside an outer wrap.
Figure 11:
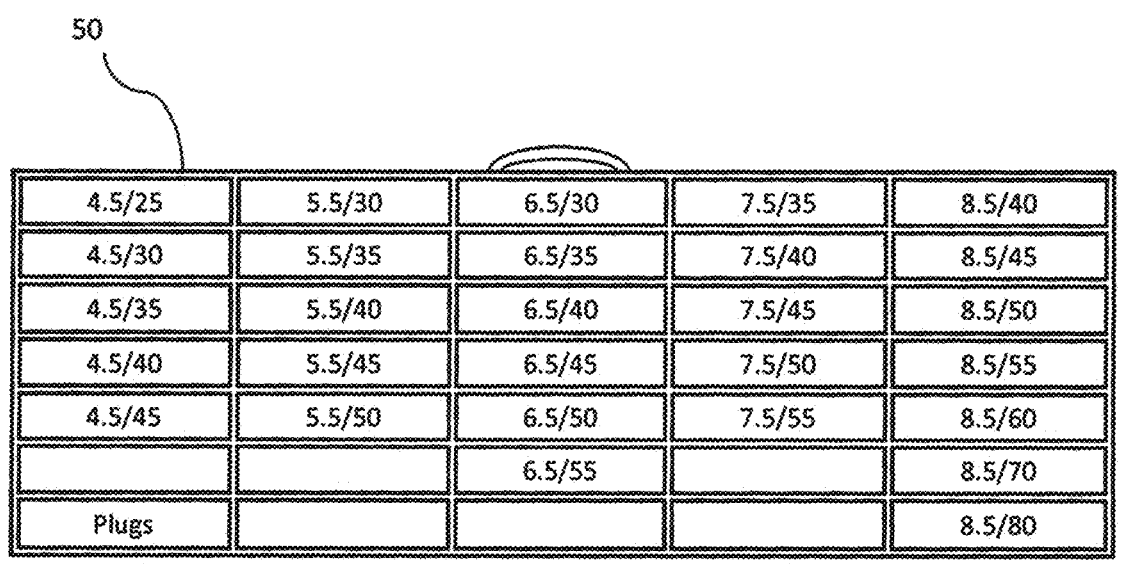
FIG. 11 is a compartmentalized storage container of wrapped, loaded pedicle screw holders.

To maintain sterility of the implant holder and the implants, two sterile screws 3 and two sterile plugs 6 are loaded into a sterile body 11 in a sterile field. FIG. 7 shows a body 11 loaded with two screws 3 and two plugs 6. The loaded sterile body 11 is encased while in a sterile field in an outer wrap 40 that will keep the body 11, screws 3 and plugs 6 sterile during storage and transport. FIG. 8 shows a body 11 loaded with two screws 3 and two plugs 6 wrapped in an outer wrap 40 of plastic. Preferably the outer wrap 40 is labeled to indicate the type of screw in the holder, by size, materials or other characteristic. Alternatively, an array of wrapped, loaded bodies can be stored in a reusable compartmentalized storage bin with each compartment labeled to indicate the type of screw, instrument, or other implant in each compartment. FIG. 11 shows a compartmentalized storage bin 50 of loaded bodies organized by pedicle screw shaft diameter and shaft length in millimeters. Each compartment can hold more than one wrapped loaded body so that multiples of screw sizes are provided for each surgery. By using labeled packages or labeled compartments the unused sterile screws are not opened unless needed and are not contaminated, so they can be provided for another surgery without the need for sterilization. This reduces waste while maintaining safety.

Figure 9:
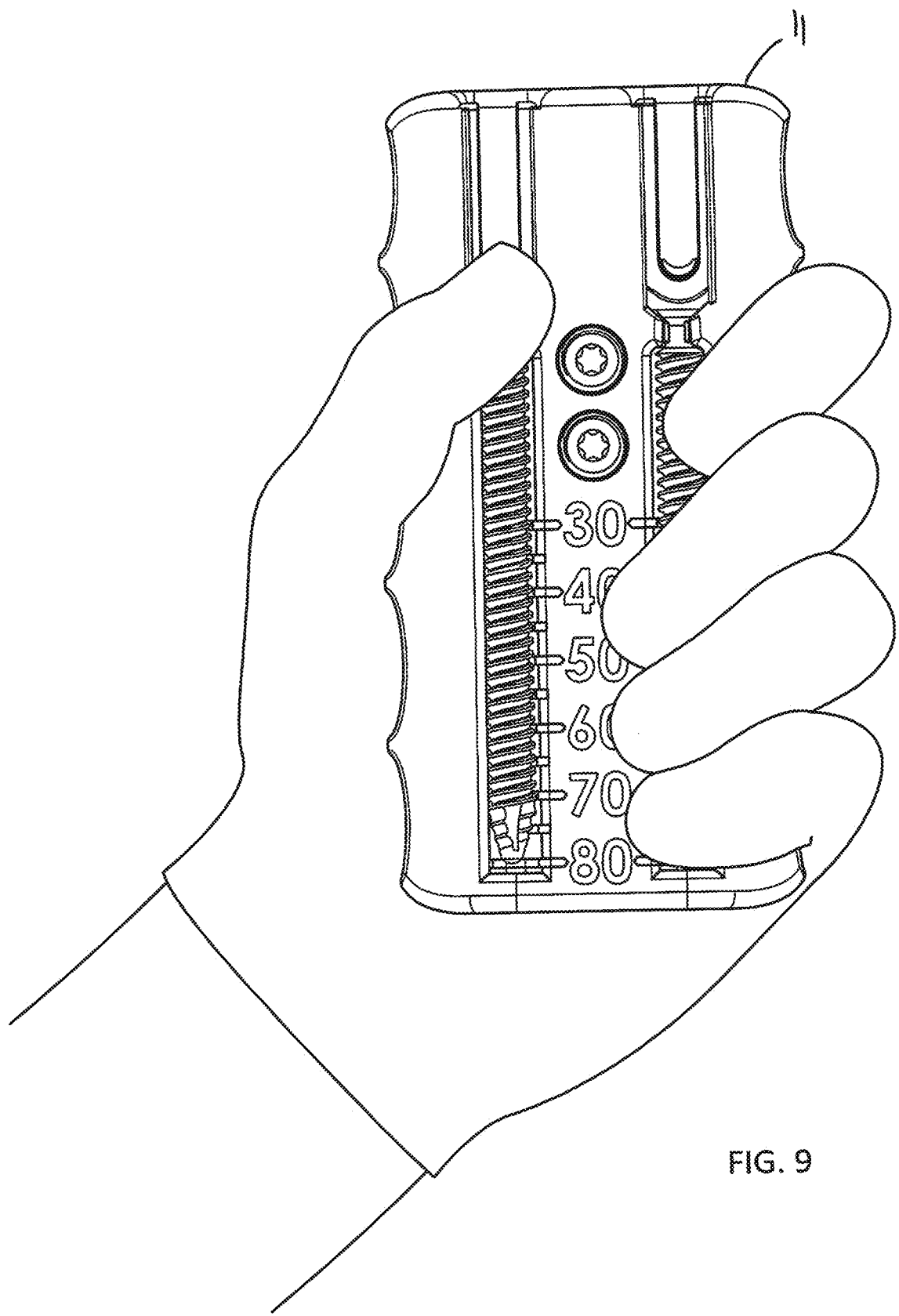
FIG. 9 illustrates the loaded pedicle screw holder of FIG. 7 held by a gloved hand.
Figure 10:
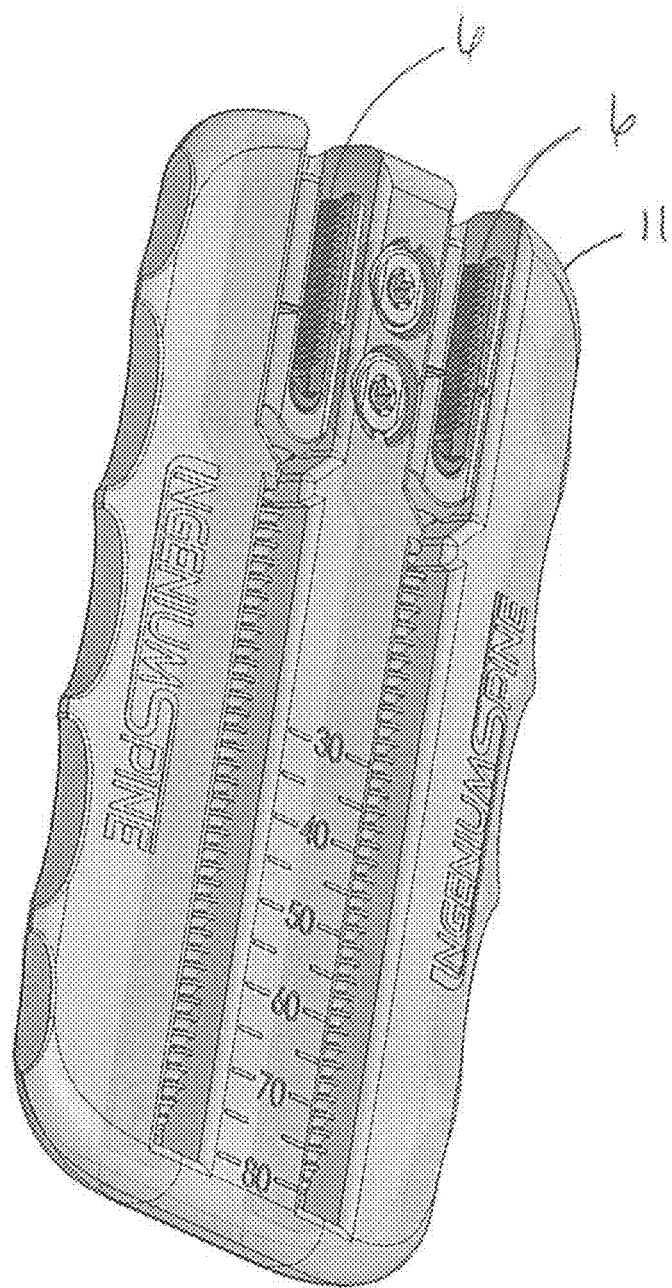
FIG. 10 is a perspective view of the loaded pedicle screw holder of FIG. 7.

The wrapped, loaded bodies 11 are transported eventually to the operating room. Inside the operating room, a surgeon instructs the surgical technician as to which size of screw is desired, and the surgical technician opens the now-contaminated outer wrap 40 to expose the loaded body. The surgical technician holds the loaded body in his or her hand, with the proximal end toward the surgeon. See FIG. 9. The surgeon screws a threaded insertion tool (not shown) into the head 5 and gently pries the screw out of the holder by deforming the holder. FIG. 10 shows the threads on the inside of head 6 of the pedicle screw that the insertion tool is screwed into. The threaded insertion tool is the same tool used to insert the pedicle screw 3 into a patient's body. In this way the surgeon retrieves the screw 3 from its container without touching the container and directly inserts the screw 3 in the patient without risking contamination: sterility is maintained for both the surgeon and the implant.

While there has been illustrated and described what is at present considered to be the preferred embodiment of the present invention, it will be understood by those skilled in the art that various changes and modifications may be made and equivalents may be substituted for elements thereof without departing from the true scope of the invention. Therefore, it is intended that this invention not be limited to the particular embodiment disclosed, but that the invention will include all embodiments falling within the scope of the appended claims.

We claim:

1. A surgical implant holding device comprising:
a) a deformable body comprising a face surface, a bottom surface, a first side, a second side opposite the first side, a distal end open to receive a mated tool to pry out the implant from the deformable body and a proximal end;
b) at least one implant-receiving cavity in the deformable body open to the face surface, wherein each implant-receiving cavity is configured to releasably hold an implant that is releasable when the deformable body is deformed; and
c) at least one grip indentation in the first side and at least one grip indentation in the second side.

2. The device of claim 1 wherein the deformable body is elastic.

3. The device of claim 1 wherein the deformable body comprises silicone.

4. The device of claim 1 wherein the deformable body has a width, a length, and a thickness and the width of the deformable body is sized to fit in a palm of a user's hand.

5. A surgical implant holding device comprising:
a) a deformable body comprising a face surface, a bottom surface, a first side, a second side opposite the first side, a distal end open to receive a mated tool to pry out the implant from the deformable body and a proximal end;
b) at least one grip indentation in the first side and at least one grip indentation in the second side; and
c) at least one implant-receiving cavity in the deformable body open to the face surface wherein:
i) each implant-receiving cavity is configured to releasably hold an implant that is releasable when the deformable body is deformed; and
ii) at least one implant-receiving cavity is the same shape as the implant.

6. The device of claim 5 wherein the implant is a pedicle screw, a set screw, a rod, a connector, a hook, or a spinal cage.

7. The device of claim 5 wherein the deformable body is elastic.

8. The device of claim 5 wherein the deformable body comprises silicone.

9. The device of claim 5 wherein the deformable body has a width, a length, and a thickness and the width of the deformable body is sized to fit in a palm of a user's hand.

10. A surgical implant holding kit comprising:
a) a sterile deformable body comprising a face surface, a bottom surface, a first side, a second side opposite the first side, a distal end open to receive a mated tool to pry out the implant from the deformable body and a proximal end;
b) an implant-receiving cavity in the sterile deformable body open to the face surface, wherein each implant-receiving cavity is configured to releasably hold an implant that is releasable when the sterile deformable body is deformed; and
c) a sterile surgical implant in the implant-receiving cavity.

11. The surgical implant holding kit of claim 10 further comprising at least one grip indentation in the first side and at least one grip indentation in the second side.

12. The surgical implant holding kit of claim 10 wherein the sterile deformable body is sealed in an outer wrap forming a wrapped sterile deformable body.

13. The surgical implant holding kit of claim 12 wherein the outer wrap is made of a material capable of keeping the deformable sterile body sterile.

14. The surgical implant holding kit of claim 12 further comprising a compartmentalized storage container containing a plurality of wrapped sterile deformable bodies.

15. The surgical implant holding kit of claim 10 wherein the sterile deformable body is elastic.

16. The surgical implant holding kit of claim 10 wherein the sterile deformable body comprises silicone.

17. The surgical implant holding kit of claim 10 wherein the sterile deformable body has a width, a length, and a thickness and the width of the body is sized to fit in a palm of a user's hand.

18. The surgical implant holding kit of claim 10 wherein the implant-receiving cavity is the same shape as the implant.

19. The surgical implant holding kit of claim 18 wherein the implant is a pedicle screw, a set screw, a rod, a connector, a hook, or a spinal cage.

* * * * *